United States Patent

Davis et al.

[11] Patent Number: 5,648,594
[45] Date of Patent: Jul. 15, 1997

[54] BIG BEND BLUEBONNET

[75] Inventors: Tim D. Davis, Plano; Wayne A. MacKay, El Paso, both of Tex.

[73] Assignee: The Texas A&M University System, College Station, Tex.

[21] Appl. No.: 424,922

[22] Filed: Apr. 19, 1995

[51] Int. Cl.⁶ .................. A01H 5/00; A01H 1/00
[52] U.S. Cl. .................. 800/200; 800/230; 47/58; 47/DIG. 1
[58] Field of Search .................. 800/200, 230; 47/58; 438/172.1

[56] References Cited

U.S. PATENT DOCUMENTS

| | | | |
|---|---|---|---|
| 3,861,079 | 1/1975 | Patterson | 47/58 |
| 4,143,486 | 3/1979 | Maan | 47/58 |
| 4,351,130 | 9/1982 | Rutger et al. | 47/58 |
| 4,594,810 | 6/1986 | Troyer | 800/200 |
| 4,626,610 | 12/1986 | Sun | 800/200 |
| 4,705,910 | 11/1987 | Price | 800/200 |
| 4,762,964 | 8/1988 | Yenson | 800/200 |

OTHER PUBLICATIONS

Poehlman "Breeding Field Crops" AVI Publishing. pp. 218–220 1987.
Hartmann et al. "Plant Propagation" Prentice–Hall pp. 159–164 1968.

*Primary Examiner*—Gary Benzion
*Attorney, Agent, or Firm*—Pravel, Hewitt, Kimball & Krieger

[57] ABSTRACT

Novel breeding lines of Big Bend Bluebonnets, *Lupinus havardii*, inbred to have the following characteristics: uniform deep color, blue, pink, or white; at least 15 harvestable racemes per plant; each raceme being at least 12 inches long; and reduced flower abscission from the uncut raceme. Methods for reproducibly growing *Lupinus havardii* in the greenhouse and methods for post-harvest treatment of cut flowers are disclosed. The new bluebonnet lines have great utility in the cut flower industry.

8 Claims, No Drawings

BIG BEND BLUEBONNET

FIELD OF THE INVENTION

This invention relates to novel breeding lines of the Big Bend Bluebonnet Texas Series (*Lupinus havardii*) produced through recurrent phenotypic selection. The novel lines have blue, pink, and white flowers, high flower yields and reduced flower abscission. The lines are successfully grown in the greenhouse according to the method of the invention with short cropping times. The plant lines of the invention are particularly useful to fill a specific need in the cut flower industry, providing a tall raceme with blue, pink, or white color, year-round.

BACKGROUND OF THE INVENTION

*Lupinus havardii* (Big Bend Bluebonnet) is a fragrant winter annual native to a narrow geographical range along the Rio Grande River in southwest Texas. The occurrence of native populations is highly variable and depends upon the amount and distribution of annual rainfall. In moist years, plants may be distributed from the desert floor to mountain slopes. In dry years, populations are restricted to the edges of roads and areas where water collects after brief rains. In some areas, populations may not be present for ten or more years because conditions are not conducive to seed germination and plant growth.

Growers of cut flowers have long attempted to culture lupine species as cut flowers, because of their beauty and fragrance. The long and durable racemes of *Lupinus havardii* and particularly those having blue flower color would fill a unique niche in the cut flower industry. Prior attempts to cultivate lupine species have generally been unsuccessful. Major limiting factors include a long cropping time, low and inconsistent flower yields, and quick flower drop from the harvested raceme. These limitations have prevented lupine species from being commercially useful as a cut flower.

The potential value of lupines in the cut flower trade and the problem of premature flower abscission is disclosed in Mohan Ram and Rao, 1977 *Scientia Hortic.* 7:377–382. In this study, the authors attempted to prolong the vaselife of *Lupinus hartwegii* Lindl by chemical treatments with only limited success. Shedron and Weiler, 1982, *HortScience* 17:807–809 documents the long production period required to obtain flowering in Russell lupines and further notes only 3–7 racemes are produced per plant. Warne, 1947, *J. Royal Hort. Soc.* 72:193–195 discloses the flower abscission problem commonly observed in lupines.

Because of the beauty and desirability of lupines in the cut flower industry, it would be highly useful to provide lupine lines having improved characteristics suitable for commercial growth, harvest, and use as a cut flower.

SUMMARY OF THE INVENTION

The Big Bend Bluebonnet Texas Series has been developed through recurrent phenotypic selection to provide blue, pink, and white-flowered lines having improved characteristics suitable for commercial growth, harvest, and use as a cut flower. The Big Bend Bluebonnet Texas Series and the claimed methods for their production overcome problems associated with prior known wildflowers and attempted greenhouse varieties of lupines and provides a crop having the following characteristics: good flower yields (an average of 15–25 harvestable racemes per plant); a relatively short cropping time (about 5 months); tall racemes (at least 12 inches at flower harvest); and minimized flower abscission.

The invention provides novel Big Bend Bluebonnet Texas Series breeding lines; seed of the inbred lines which produces a uniform crop and which can be used for continued selection to obtain final novel varieties which breed true for uniform color (blue, pink, or white), tall racemes, more than 15 harvestable racemes per plant, good flower spacing on racemes, and reduced flower abscission; and cut flowers of the inbred lines having these desired characteristics. and providing commercially useful *Lupinus havardii* lines.

Methods for breeding useful *Lupinus havardii* (Big Bend Bluebonnet) plants in the greenhouse by recurrent phenotypic selection result in lines that are uniform in color, possess thick racemes, and have a greater number of harvestable racemes per plant as well as increased retention of flowers on the raceme. Methods for preparing seed by specific acid scarification techniques ensure uniform and shortened germination times (e.g. about 5 days or less) enabling the plants to be easily and reproducibly grown in the greenhouse. Methods for growing the plants include specific growth conditions such as a well drained and well aerated media having a neutral to slightly basic pH. Post-harvest handling methods, including immediate immersion in a solution of silver thiosulfate permit longer storage times and a longer average vaselife of the cut flowers.

DETAILED DESCRIPTION OF THE PREFERRED EMBODIMENTS

I. Phenotypic Selection Methods

The claimed lines of Bluebonnet Series of the instant invention, having commercially useful characteristics, are produced by recurrent phenotypic selection. In general, this method involves identification of wild plants having a desired characteristic, obtaining seed from the wild plants, and growing plants through at least two (2) cycles of recurrent phenotypic selection to improve the desired genetic traits. To produce a plant line having a desired color, wild plants possessing color traits that would be expected to yield the desired color upon selection are chosen. The plants are then grown through multiple cycles of recurrent phenotypic selection, choosing those plants that progress toward the desired color.

After the first cycle to select color, selection during subsequent cycles is made for uniform color, raceme strength (e.g. thickness), raceme height, high numbers of harvestable racemes per plant, reduced flower abscission, and minimal spacing between flowers in raceme (e.g., less than about one centimeter).

This selection process is continued through subsequent cycles using the same selection criteria until the population reaches about 95% uniformity for the desired traits and these traits breed true.

Using these methods as further described below in the Examples, breeding lines having a uniform blue, pink, or white color with at least 15 harvestable racemes per plant, good spacing of flowers on the raceme and reduced flower abscission at harvest have been developed through three selection cycles. Seed collected after two selection cycles was placed on deposit at the American Type Culture Collection (B-2, P-2, and W-2). Continued selection cycles as described above will result in a population of about 95% uniformity for the desirable traits enumerated above, which population breeds true for these characteristics. Racemes obtained from the deposited seed and from the seed collected from additional selection cycles are useful as cut flowers, providing unique and uniform blue, pink, and white-colored cut flowers having good storage and shipping characteristics, strong and long racemes, with good flower spacing on the raceme and reduced flower abscission.

II. Method for Growing Plants

Seed of three distinct color breeding lines of *Lupinus havardii* (Big Bend Bluebonnet) has been deposited in the American Type Culture Collection (ATCC), Rockville, Md. 20852. The deposited seed was collected from cycle 2 breeding lines and includes B-2 (blue) having ATCC accession number 97115; P-2 (pink) having ATCC accession number 97116; and W-2 (white) having ATCC accession number 97117.

The seed of the *Lupinus havardii* is hard-seeded and able to survive long storage times (e.g., years). Prior to planting, the seed is prepared by scarification. Several methods of scarification are known to improve germination of hard-seeded species. For example, immersion in concentrated sulfuric acid, mechanical abrasion methods, and the like. A preferred method for scarifying seed of *Lupinus havardii* is to immerse seed in concentrated sulfuric acid for about 90 to 180 minutes, as shown in the Examples below. The acid-treated seeds are then washed in water and dried.

The prepared seeds are planted in a well drained and well aerated medium such as a mixture of peat moss and perlite at a soil pH that is near neutral, e.g., neutral to slightly acidic. Suitable commercially available media include (METRO-MIX®200) (a growing medium containing choice cut Canadian Sphagnum Peat Moss, #3 grade horticultural vermiculite, tested wetting agent, starter nutrient charge, horticultural perlite and selected washed granite sand) (Grace-Sierra, Milpitas, Calif.) and (SUNSHINE MIX NO. 4) (a planting mix developed for conditions that require higher air capacity and faster drainage) (SunGro, Bellview, Wash.). Bark-based media do not appear to be suitable, presumably due to pH problems. Care should be taken not to overwater the medium. For example, the surface of the medium should be allowed to dry between waterings.

Seedlings should be grown in pots, e.g., about 3 gallon is preferred. Plants begin to flower after about ten weeks from planting. Greatest flower production occurs about 4-5 months from planting, under a daily maximum temperature of about 23°-29° C. (75°-85° F.). Flower harvest may continue for longer periods. The best quality racemes are produced under full sun conditions, e.g., unshaded.

Seedlings may be fertilized, e.g., with nitrogen, phosphorous, and potassium, using a constant liquid nutrient solution (applied at each watering), a slow release formulation, or other known application methods.

For optimal germination, planted seeds should be maintained at a temperature of from about 21° C. to about 33° C. For most rapid and uniform germination, the temperature range is preferably about 24° C.-29° C. Seedlings emerge within 3-4 days of planting under these optimal conditions.

III. Harvesting

To maximize the yield of useful flowering racemes, at harvest, racemes should be cut above sub-tending buds, that is, above any axillary racemes developing at the base of the cut raceme. In this way, the axillary racemes will continue to grow and yield additional harvestable racemes.

IV. Post-Harvest Treatment

Upon harvest, racemes are preferably immediately placed in a solution of silver thiosulfate (STS). As shown in the Examples, immersion in a solution of about 40-80 mg/l for about four hours significantly prolongs vaselife, and inhibits flower abscission from the cut racemes. The treatment time may be reduced by increasing the silver thiosulfate concentration, e.g., about 700 mg/liter for about one hour may be used. After treatment, the racemes can be transferred to water or moistened floral foam for storage or immediate display. Alternatively, the treated racemes can be stored at cool temperatures, e.g., about 5° C., in water or dry for up to 72 hours. The dry stored racemes are recut and rehydrated without significant reduction in vaselife. Racemes may be dry packed and air-shipped with minimal loss of commercially useful product. The average vaselife of the claimed flowers treated with STS is about 10-12 days, in contrast to untreated flowers which have a vaselife of about 5-7 days.

EXAMPLES

The following examples illustrate the methods for producing the claimed invention and are not limiting.

Example 1

Recurrent Selection of Blue *Lupinus havardii* (Big Bend Bluebonnet)

About 100 seeds were collected from a wild population of *Lupinus havardii* (Big Bend Bluebonnet) having uniform blue color located approximately 4.6 miles west of Lajitas, Tex. in April-May. The seeds were scarified in concentrated sulfuric acid for 120 minutes, washed with water, dried, packed in paper, and stored at 4° C. Seeds were planted the following October in outdoor plots of sand soil, Blue Point soil type, which is a fine, sandy unclassified loam. Plants were rogued after flowering, removing plants not having a dark blue color, having less than 10 racemes, or having poor stem strength. The twenty remaining plants were open pollinated by bees and cycle-1 seed was collected from late April to early May.

The following late January, 900 cycle-1 seeds were direct seeded in 300 three gallon pots in the greenhouse. The pots contained (SUNSHINE MIX NO. 4) (a planting mix developed for conditions that require higher air capacity and faster drainage) and were fertilized with (PETERS PROFESSIONAL® GENERAL PURPOSE FORMULAS GENERAL PURPOSE (20-20-20))(a general purpose fertilizer that is acidic with a nitrogen source that is largely ammoniac) (Grace Sierra, Milipitas, Calif.), a 20-20-20 mixture of N, P, K. The fertilizer was introduced to the soil by constant liquid nutrient solution, e.g., applied with each watering. The temperature of the greenhouse was regulated to a minimum of 50° F. at night and maximum of 85°-90° F. in daytime. Plants were grown in full sun. At about 30 days post-planting, one seedling per pot was retained, based on plant vigor. At about 14 weeks, selection was made choosing those plants having a uniform dark blue color, good raceme thickness, 20-25 racemes per plant, total plant height of between two and three feet, minimal flower abscission on the uncut raceme, and less than about one centimeter spacing between flowers on raceme. Any plants showing signs of poor health including foliar disease, insect infestation, or chlorosis were rogued. The ten best plants of the 300 grown were selected and randomly intercrossed by hand-pollination using an artist's paintbrush. Cycle-2 seed was collected in June, cleaned and stored.

In August, the stored cycle-2 seed (900 seed) was scarified and direct seeded as described above, following the same growth and selection procedures described above. In November, ten plants were selected of the 300 grown. Cycle-3 seed was collected, cleaned, and stored.

Cycle-2 seed was deposited at the ATCC and was given accession No. 97115.

Example 2

Recurrent Selection of White *Lupinus havardii* (Big Bend Bluebonnet)

*Lupinus havardii* plants exhibiting near-white flower color (white to pale blue) were tagged in an arroyo near Lajitas, Tex. Five seeds were collected from these plants in May. These five seeds were scarified in concentrated sulfuric acid as described for Example 1, direct-seeded into five three-gallon pots, and grown under the greenhouse conditions as described for Example 1. Four white plants produced from this seed were selected and hand-pollinated. Cycle-1 seed was collected, washed, dried and stored at 4° C. as described for Example 1.

In December, 900 cycle-1 seeds were scarified, direct-seeded into 300 pots, and grown as described for Example 1. Plants were selected for three lines in March on the basis of white color. One single white plant had a "creamy white" color, e.g., not paper white, but near egg shell white. Six plants had a yellow eye spot that failed to turn red on pollination. Six other plants retained the normal yellow eye spot which turned red upon pollination. Cycle 2 seed from each of these white color lines was produced and collected as described for Example 1.

In August, 288 cycle-2 seed of each of the three white lines was direct seeded into cell-pack trays (72 cell flat) containing the same medium as used above, two seeds per cell-pak. About one month after planting, 100 of each line's seedlings were selected for vigor and transplanted into three gallon pots. Plants were grown as described above and selection made in November. All plants from the egg shell color line were discarded because they lacked sufficient height, strength, and general vigor. The two eye spot lines showed no distinction based on eye spot and were subsequently bulked. Plants were selected using the criteria of good white color, stem strength, greater than 15 racemes per plant, minimal flower abscission on the uncut raceme, and good flower spacing on the raceme. The selected bulked plants were randomly intercrossed by hand pollination and cycle-3 seed was collected, cleaned and stored.

Cycle-2 seed was deposited at the ATCC and was given accession No. 97117.

Example 3

Recurrent Selection of Pink *Lupinus havardii* (Big Bend Bluebonnet)

A *Lupinus havardii* plant exhibiting a pink flower color was tagged in Lajitas, Tex. Seven seeds were obtained from this pink-flowering plant in the spring. After scarification, the seven seeds were direct seeded into 3-gallon pots in the fall according to the greenhouse conditions and methods described for Example 1. Only one of the plants grown from these original seeds had pink flowers while the others all displayed blue flowers. This plant was self-pollinated upon flowering and cycle-1 seed was collected, cleaned, and stored as described for Example 1. The blue plants were self-pollinated and were also backcrossed to the pink-flowering plant by collecting pollen from the pink-flowering plant and transferring it to the blue-flowering plants (the pink-flowering plant was the male parent in the cross). Cycle 1 seed was collected, cleaned, and stored.

In the fall, three seeds were direct seeded into 300 three-gallon pots using seed collected from the self-pollinated pink plant. Seedings were thinned to one plant per pot approximately 30 days after seeding. There were eleven blue plants (blooming the first week of November) in the population that were discarded. The remaining plants were pink (blooming week of Thanksgiving). Ten plants were selected from these pink-flowering plants based upon the selection criteria of good pink color and the desired plant and flower characteristics as described for Example 1. The remaining 279 plants were discarded. One plant was reselected as best of the ten and self-pollinated. The remaining nine plants were intercrossed. Cycle 2 seed was collected, cleaned, and stored.

In the fall, cycle 2 seeds from the single pink-flowering plant self-pollinated the previous year were seeded into eight 1072 trays (12 packs with six cells per pack) with two seeds per cell. Approximately one month after seeding the seedlings were transplanted to 300 three gallon pots. Two weeks following transplanting, seedlings were thinned to one per pot. The remaining cell packs were retained and monitored until flowering. All plants in the cell packs were pink-flowered. Three groups of plants were selected from the three gallon pots. They had the following characteristics: Group 1 consisted of four plants with a deeper more intense pink flower color; Group 2 consisted of four plants with a light pink flower color; Group 3 consisted of four plants with a pink banner and a slight blue coloration in the predominately pink keel, i.e., a weak blue/pink bicolor. Each group was independently pollinated. Cycle 3 seeds from each group were collected, cleaned, and stored separately.

Cycle 2 seed of the self-pollinated plant was deposited at the ATCC and was given Accession No. 97116.

Example 4

Evaluation of Seed Scarification Methods

Like many legumes, *Lupinus havardii* produces hard seed coats that are impervious to water. Studies with related Lupinus species suggest scarification, e.g., with sulfuric acid is needed to promote germination. The efficacy of various seed scarification methods in promoting germination was evaluated.

Seed was collected from *Lupinus havardii* plants grown in field plots at the Texas A&M Research and Extension Center in El Paso. Seed was prepared as follows:

1) Acid scarification: seed was placed in concentrated (36N) sulfuric acid (60 seed per 50 ml) for a period of time ranging from 0–150 minutes. The treated seed was thoroughly rinsed with distilled water before sowing.

2) Water soak: seed (25 per treatment group) was untreated (control) or soaked in water for 24 hours. The water treatment groups included room temperature tap water (22° C.) and tap water ranging from 60° C.–100° C., the water being heated to temperature prior to addition of seed and thereafter permitted to cool for 24 hours.

3) Mechanical scarification: a razor blade was used to pierce the seed coat.

After treatment, seed was placed in clear petri dishes and transferred to a growth chamber having a 12 hour photoperiod and a day/night temperature regime of about 25°/20° C. Germination was monitored daily for seven days after which no further germination occurred. Each experiment was repeated three times. Data was calculated as the percent germination for each experiment, and the mean of the three experiments is reported in the data tables.

Results:

Without scarification, less than 20% of the seeds germinated within one week (Table 1). Germination percentages increased sigmoidally as scarification time in concentrated sulfuric acid increased. Germination was almost 100% one week after placement in sulfuric acid for 120 minutes. The time required for optimum germination of Lupinus (90–120 minutes) is significantly greater than that needed for other lupines (45–60 minutes).

Nicking the seed coat with a razor blade also resulted in 100% germination after one week. However, soaking seed in water for 24 hours failed to promote seed germination regardless of water temperature (Table 2).

TABLE I

ACID SCARIFICATION

| SCARIFICATION TIME (MIN) | GERMINATION (%) AT 7 DAYS |
|---|---|
| 0 | 16 |
| 15 | 33 |
| 30 | 41 |
| 45 | 46 |
| 60 | 71 |
| 75 | 82 |
| 90 | 89 |
| 120 | 96 |
| 150 | 98 |

TABLE 2

Water soak treatment

| TREATMENT | GERMINATION % AT 7 DAYS |
|---|---|
| Untreated control | 10.6 |
| 22° C. | 9 |
| 60° C. | 15 |
| 80° C. | 11.8 |
| 100° C. | 9.8 |

Example 5

Effect of Temperature on Germination

Temperature effects on seed germination were studied using seed that had been scarified in concentrated sulfuric acid for 90 minutes. Five replicate groups of 45 seeds each were imbibed in deionized water for 30 minutes at room temperature for the high temperature (18°–35° C.) studies. Seeds in the lower temperature (10°–18° C.) studies were not subjected to the water pretreatment.

Seeds were placed on one sheet of Whatman 4 filter paper (Whatman Paper, London) in 100×15 mm Pyrex petri dishes and moistened with 2 ml deionized water. The dishes were sealed with parafilm and placed on a thermogradient plate. Deionized water was added as needed to maintain constant moisture during the experiments.

The petri dishes were arranged five per column (replications) perpendicular to the temperature gradient on a thermogradient plant. The aluminum thermogradient plate measured 61×122×2.5 cm (width/length/thickness) and was insulated on the bottom and sides. A 30× 30 cm heat plate in contact with the bottom surface at one end provided heat, and compressed freon circulating through eight 6.4 cm diameter lateral holes in the opposite end cooled the plant. A photoperiod of 16 hours was provided by two cool-white fluorescent bulbs positioned 40 cm above the plate surface. Each experiment was conducted three times.

A thermocouple was placed in the bottom of an empty petri dish on each temperature column. Temperature was recorded every 30 minutes by a datalogger for the duration of each test. Daily temperature variation occurred within the plate with changes in room temperature, however, the temperature varied less than 1.5° C. with no overlap between the columns.

Germination, defined by the presence of a radicle at least 2 mm in length, was counted daily for seven days in the lower temperature regime (10°–18.3° C.) and at two hour intervals for 28 hours at the higher temperatures (18°–35° C.) after which time no further germination occurred.

Results

Germination occurred rapidly on the thermogradient plate within the higher temperature range (Table 3). Seed germination was greater than 50 percent ten hours after placement on the thermogradient plate for the 23.9°, 26.7°, and 29.4° C. treatments and within 16 h approximately 90 percent of the seed germinated in the 26.7° and 29.6° C. treatments. At the end of the experiment (28 h), seed in all but the highest and lowest temperature treatments had reached 90 percent or greater germination. Seed placed in the lowest temperature treatment (18.3 ° C.) exhibited delayed germination with less than 30 percent of the seed germinated at 16 h compared to the 21.1° C. treatment wherein approximately 60 percent of the seed had germinated. After 28 h the germination percentage at 18.3° C. was approximately 80 percent. Seeds placed in the highest temperature treatment (35° C.) also exhibits delayed germination with a much reduced final germination percentage (less than half of the seed germinated). More importantly, seed and seedling necrosis was already becoming apparent in this treatment after 28 h. The roots were characterized by browning, and discoloration of the filter paper was apparent around each seed regardless of radicle emergence.

TABLE 3

Temperature on Germination

| TIME | Germination (%) | | | | | | |
|---|---|---|---|---|---|---|---|
| (hours) | 18.3° C. | 21.1° C. | 23.9° C. | 26.7° C. | 29.4° C. | 32.2° C. | 35° C. |
| 4 | 0 | 0 | 0.2 | 0 | 0.1 | 0 | 0 |
| 6 | 0 | 0.3 | 3.3 | 15.1 | 17.7 | 9.3 | 0 |
| 8 | 0.5 | 4.3 | 29.8 | 54.2 | 46.3 | 24.9 | 1.6 |
| 10 | 1.5 | 22.5 | 59.8 | 73.5 | 64.9 | 39.5 | 4.9 |
| 12 | 7.8 | 39.1 | 71.3 | 83.8 | 79.1 | 53.1 | 8.6 |
| 14 | 14.9 | 46.9 | 81.7 | 89.1 | 86 | 62.2 | 12.4 |
| 16 | 24.2 | 59.9 | 86.7 | 92.5 | 90.3 | 77.4 | 17.6 |

TABLE 3-continued

Temperature on Germination

| TIME | Germination (%) | | | | | | |
|---|---|---|---|---|---|---|---|
| (hours) | 18.3° C. | 21.1° C. | 23.9° C. | 26.7° C. | 29.4° C. | 32.2° C. | 35° C. |
| 24 | 70.1 | 87.8 | 94.8 | 96.7 | 96.6 | 90.4 | 46.3 |
| 28 | 82.3 | 90.4 | 95.4 | 96.8 | 96.9 | 91.2 | 50.6 |

There was an inverse relationship between temperature and radicle growth (data not shown). Radicle growth decreased as temperature increased while hypocotyl elongation increased with increasing temperature. Seedlings transplanted from the two highest temperature treatments (32.2° and 35° C.) failed to survive. Seeds from all other temperature treatments emerged within three days and produced normal seedlings.

The seed necrosis, lack of germination, and failure of seedlings to survive transplanting in the 32.2° and 35° C. treatment can be overcome by lowering the night temperature. In experiments conducted in a seed germination chamber using the average daily high and low temperatures (37°/23° C., 12 hours each) for the month of August in the Big Bend area of Texas, approximately 90 percent of the seed germinated and grew with no signs of necrosis present (data not presented). Additionally, there was no difference in the seed germination percentage and little difference in seedling growth between the August average high/low daily temperature regime and that of September (34°/19° C.) and October (30°/13° C.). In the study comparing light and dark treatments there was no difference in seed germination percentage between light and dark treatments (87 and 88 percent, respectively) or seedling growth for the first 48 hours (data not shown). Thus light is not required for seed germination in this species.

Individual experiments were conducted to evaluate the effects of temperature on radicle and hypocotyl growth. Using the thermogradient plate and the higher temperature treatments described above, (15 seed per petri dish), radicles and hypocotyls were measured daily for five days. After five days, seedlings were transplanted to pots and grown in the greenhouse.

In addition, seed was placed in a germination chamber using the average day/night temperatures in the Big Bend area of Texas for the months of August (37°/23° C.), September (34°/19° C.), and October (30°/13° C.). Light was provided by fluorescent lamps (~20 μmols$^{-1}$m$^{-2}$ in the center of the shelf). Ten petri plates with fifteen seeds per plate, with half of the plates wrapped in aluminum foil to exclude light, were placed in the germination chamber for five days. Radicles and hypocotyls were measured daily and germination percentages calculated. Temperature treatments were conducted separately with each day/night temperature regime tested three times.

Germination in the lower temperature range experiments on the thermogradient plate proceeded slowly but at the conclusion of the experiment the maximal germination percentages were comparable to those in the higher temperature regime experiments. Seed germination did not reach 90 percent or greater until 120 hours for the three higher temperature treatments (12.8°, 15.6°, and 18.3° C.) (Table 4). Germination was about 85 percent for seed in the lowest temperature treatment (10° C.) after 168 hours. All temperature treatments produced normal seedlings when transplanted to soil. After 24 hours, germination percentage of seed placed in the 18.3° C. treatment was not comparable to the thermogradient plate experiment with the higher temperature range. This was probably due to the lack of imbibition prior to placement on the thermogradient plate in the lower temperature regime experiment.

TABLE 4

Temperature effects on Germination

| TIME | Germination (%) | | | |
|---|---|---|---|---|
| (hours) | 10° C. | 12.8° C. | 15.6° C. | 18.3° C. |
| 24 | 0 | 12.5 | 24.2 | 47.9 |
| 48 | 0.9 | 43.3 | 85.6 | 93.3 |
| 72 | 8.1 | 78.2 | 96.2 | 94.7 |
| 96 | 29.3 | 91.5 | 96.7 | 94.9 |
| 120 | 57.1 | 94.2 | 96.7 | 94.9 |
| 144 | 80.2 | 94.2 | 96.7 | 94.7 |
| 168 | 86.7 | 94.2 | 96.7 | 94.7 |

Our results suggest that optimum seed germination for *Lupinus havardii* requires a minimum 90 to 120 minutes sulfuric acid scarification period. The most rapid gemination occurs in a temperature range of 24°–29° C. Nonetheless high germination percentages can be obtained over a relatively wide temperature range. Indeed, our data suggest that temperature does not limit germination in the native habitat throughout much of the year. The two main factors which appear to limit germination are lack of moisture and the impervious seed coat.

Example 6

Evaluation of Soils

*Lupinus havardii* seedlings germinated in 1072 trays were transplanted into three gallon pots filled with five different soilless mixes in December. All plants were thinned to one seedling per pot about one month post transplant. Fertilizer was applied at each watering at a rate of 100 ppm (20-20-20 NPK Peters General purpose soluble fertilizer). Plants were grown in the greenhouse in full sun with a minimum night temperature of 10° C. and a daily maximum of about 29° C. Watering and fertilizing were done as described for Example 1.

The data reported in Table 5 were obtained at about four months post-planting (April), e.g., prior to completion of flower production for the control group, Sunshine No. 4.

Results of the potting media experiments are shown in Table 5, and indicate that artificial soils that have a high bark content (Metro Mix 720 and the local nursery mix) or have poor aeration qualities (the two Grace Sierra mixes) do not support growth of *Lupinus havardii* as well as the control treatment of Sunshine No. 4 which is a coarse peat moss based soilless media.

The local nursery mix had a high death rate of plants (32% of the plants died) even after selecting vigorous seedlings upon transplanting and thinning. Although the surviving plants produced a modest number of racemes (5.5 on average), when combined with the high mortality rate, the resulting crop would not be competitive with the control treatment of at least 15.5 racemes per plant (or at the end of the harvest period, the expected 20–25 racemes per plant). Clearly the other mixes are inferior for production since few or no racemes are produced and no commercial crop could be produced.

TABLE 5

| Soilless Mix | Number of Plants | Number of plants that died | Average Racemes/plant |
|---|---|---|---|
| Grace Sierra 1 | 20 | 2 | 0.4 |
| Grace Sierra II | 20 | 5 | 0.25 |
| Local Nursery Mix | 50 | 16 | 5.5 |
| Metro Mix 720 | 20 | 0 | 0.005 |
| Sunshine No. 4 | 40 | 0 | 15.5 |

Example 7

Effect of Photoperiod and Chilling on Flowering

The need for specific environmental conditions to induce flowering such as critical daylengths and chilling temperatures is an important consideration for floricultural crops grown in a greenhouse environment. Accordingly, experiments were conducted at the North Carolina State University Phytotron (Southeastern Plant Enviornmental Laboratory) to determine the effects of photoperiod and chilling on flowering.

Blue, Cycle-1 seed (B-1) was scarified and grown as described above for Example 1 under greenhouse conditions. Daylight was extended using incandescent lamps to achieve photoperiods of 10, 11, 12, 13 and 14 hours. To test the effects of chilling, six-week seedlings were placed at 4° C. for three weeks with a 12 hour photoperiod. The number of flowers per plant as well as the timing of the first flower appearance was observed and recorded.

The results of these experiments clearly indicated that there is no obligate photoperiod requirement for inducing flowering in the Texas Series Big Bend Bluebonnet. In addition, chilling temperatures (i.e., vernalization) are not required to induce flowering.

Example 8

Post Harvest Treatment

The effect of post harvest treatments and storage methods on the vaselife of the Texas Series Big Bend Bluebonnets were studied.

Materials and methods

Racemes of Lupinus havardii were produced in an unshaded glasshouse from November to May. Plants were grown from scarified seed in cell packs (48 cells per flat) and transplanted to 12 liter plastic pots (25 cm diameter, 25 cm height) after one month. The growing medium was (METRO-MIX®200) (a growing medium containing choice cut Canadian Sphagnum Peat Moss, #3 grade horticultural vermiculite, tested wetting agent, starter nutrient charge, horticultural perlite and selected washed granite sand) (Grace Sierra, Milpitas, Calif.) and each plant was fertilized with (SIERRA 17-6-12 PLUS MINORS) (a controlled release fertilizer containing primary, secondary and minor nutrients) (Grace Sierra) at 36 g/pot (6.1 g N/pot). Racemes began reaching harvest stage about 2.5 months after sowing and harvesting continued for 2–2.5 months thereafter. Racemes were harvested in the morning (generally from 0900–1100 hours) when they reached 40–50 cm in length and had 30–40 open flowers. Staggered plantings were used so that a constant supply of flowers was available during the experimental period. No differences in flower quality, vaselife, or abscission were observed during this time. Greenhouse temperature during production was 25° C.–30° C. during the day and 13° C.–18° C. at night. Four separate experiments were conducted with the harvested racemes:

Silver thiosulfate (STSC) experiment. Immediately following harvest inflorescences were placed in an aqueous solution of 0, 40, 80, or 160 mg/liter STS for 4 hours. During this period, the inflorescences were kept in a growth chamber at 24° C. and 20±5 µmol/m²s photosynthetically active radiation (PAR). Following STS treatment, inflorescences were placed in vases containing water.

Floral foam/preservative experiment. Immediately following harvest, inflorescences were placed in an aqueous solution of 80 mg/liter STS for 4 hours under the same conditions as for the STS experiment described above. Following STS treatment, the inflorescences were:

a) transferred to vases containing water or 9 g/liter Oasis® floral preservative (Smithers-Oasis, Kent, Ohio) or b) inserted into Oasis® floral foam (Smithers-Oasis, Kent, Ohio) moistened with water or 9 g/liter Oasis® flower preservative. The floral preservative dosage followed label recommendations. Preliminary trails indicated that the floral preservative had little effect on postharvest performance of inflorescences not treated with STS. Therefore, only STS-treated inflorescences were used for this experiment.

Storage experiment. Immediately following harvest, inflorescences were placed in an aqueous solution of 80 mg/liter STS for 4 hours under the conditions described in the STS experiment. After STS treatment, the inflorescences were:

a) placed in vases containing water (unstored control);

b) placed in vases containing water and stored in a dark cold room at 5° C. for 72 hours (wet storage) or;

c) placed horizontally in a cardboard box, covered with paper towels which were lightly sprinkled with water and then stored in a dark cold room at 5° C. for 72 hours (dry storage). Following storage, the inflorescences were re-cut and placed in vases containing water.

Color line comparison. Inflorescences were harvested from the blue-, pink-, and white-flowered breeding lines described above. Immediately following harvest, inflorescences were placed in an aqueous solution of 80 mg liter$^{-1}$ STS for 4 h under the conditions described in the STS experiment. Thereafter inflorescences were kept in vases filled with water.

Following treatment, all racemes were held in a growth chamber at 24° C. with a 16 hours photoperiod and a PAR level of 20±5 µmol/m²s provided by cool white fluorescent lamps. The number of flowers abscised was counted daily for each treatment. Vaselife was considered complete when less than 8 cm of the inflorescence contained fresh flowers (about 10–12 fresh flowers remaining). All experiments were conducted at least three times with at least 7 inflorescences per treatment.

Results and discussion:

Flower abscission began to occur 2 days after harvest from the inflorescences not treated with STS (Table 6).

Flower abscission from these inflorescences was quite high within 3–4 days after harvest. Thereafter, flower abscission subsided but the lowermost remaining flowers on the inflorescence began to dry and shrivel. Also, 5–10 new flowers opened per inflorescence during the first week after harvest. Nonetheless, after 7 days only about 8 cm of the inflorescence contained fresh flowers (Table 7). With all of the STS-treated inflorescences, flower abscission was delayed and was much less than the control (Tables 7–8). Over the first week following harvest, 13 flowers abscised per inflorescence in the controls whereas less than 3 flowers abscised per STS-treated inflorescence (Table 7). Vaselife was extended 3–5 days by the STS preconditioning treatments. Thus, a STS preconditioning treatment immediately following harvest was effective in extending the vaselife of cut inflorescences of Lupinus havardii. Following preconditioning with 80 mg/liter STS, inflorescences of Lupinus havardii had a vaselife of about 10 days when placed in either water alone or floral foam moistened with water (data not shown). Also, flower abscission was low (less than 3 flowers abscised per inflorescence) regardless of whether the inflorescences were kept in water or floral foam, thus, both water and floral foam are suitable media for displaying cut inflorescences of Lupinus havardii. The addition of the floral preservative to either of these media had no influence on flower abscission or vaselife (data not shown).

Cut inflorescences stored at 5° C. in water for 72 hours in the dark appeared in good condition at the end of the storage period and were visually indistinguishable from freshly cut inflorescences. No flower abscission occurred during storage. The inflorescences stored dry at 5° C. were noticeably wilted after 72 hours. By that time, the paper towels covering the inflorescences had become dry. However, after being recut and placed in water, the inflorescences regained turgor within about 90 minutes. This ability to rehydrate was quite impressive and might be related to the fact that this species is native to an arid region. Flower abscission and vaselife were unaffected by storage in water at 5° C. for 72 hours (Table 7). Dry storage at 5° C. for 72 hours reduced vaselife by about 2 days but did not affect flower abscission. The results of our storage experiment indicate that cut inflorescences of Lupinus havardii are amenable to storage for up to 72 hours without practical reductions in postharvest quality and vaselife.

Vaselife was the same (about 10 days) for the blue-, pink-, and white-flowered breeding lines (data not shown). Thus, recurrent phenotypic selection for novel flower color has not inadvertently altered postharvest characteristics of the inflorescences.

Taken together, our results demonstrate that cut inflorescences of Lupinus havardii have several desirable postharvest qualities, e.g., reasonable vaselife when treated with STS; ability to be stored; good performance in water or floral foam. Postharvest flower abscission is also controlled.

TABLE 6

| Days post harvest | NO FLOWERS ABSCISED/RACEME | |
|---|---|---|
| | Control | STS |
| 0 | 0 | 0 |
| 1 | 0.6 | 0 |
| 2 | 5.5 | 0 |
| 3 | 4.2 | 0.3 |
| 4 | 2.0 | 0.5 |
| 4 | | |

TABLE 7

POSTHARVEST TREATMENT

| | STS TREATMENT (MG/LITER) | | | | |
|---|---|---|---|---|---|
| Characteristic | 0 (control) | 40 | 80 | 160 | Signif. |
| No. flowers abscised per inflorescence$^z$ | 13.4 | 1.0 | 2.6 | 1.4 | Q$^y$ |
| Vaselife$^x$ (days) | 7 | 12 | 11 | 10 | Q |

$^z$during first 7 days following harvest
$^y$treatment effects were quadratic (Q) at P = 0.05 as determined by polynomial regression analysis (n ≧ 22).
vaselife considered complete when less than 8 cm of the inflorescence contained fresh flowers (10–12 flowers remaining).

TABLE 8

POSTHARVEST TREATMENT

| | STORAGE TREATMENT | | |
|---|---|---|---|
| Characteristic | Control (unstored) | Stored in water | Stored dry |
| No. flowers abscised per inflorescence$^z$ | 1.0a$^y$ | 1.0a | 1.5a |
| Vaselife$^x$ (days) | 10a | 9ab | 8b |

$^z$during first 7 days following harvest (control) or storage.
$^y$means in rows with a common lower case letter are not significantly different at the 5% level as determined by Scheffe test (n = 41)
vaselife considered complete when less than 8 cm of the inflorescence contained fresh flowers (10–12 flowers remaining).

We claim:

1. A Big Bend Bluebonnet Texas Series of Lupinus havardii, consisting of at least three distinct color lines, characterized in having at least 15 racemes per plant; the racemes being at least 12 inches in height and having reduced flower abscission compared to wild-grown plants, and each color line having a uniform color.

2. A line of the plant series of claim 1 having a uniform blue flower color.

3. A line of the plant series of claim 1 having a uniform pink flower color.

4. A line of the plant series of claim 1 having a uniform white flower color.

5. The plant line of claim 2 produced from seed having ATCC accession No. 97115.

6. The plant line of claim 3 produced from seed having ATCC accession No. 97116.

7. The plant line of claim 4 produced from seed having ATCC accession No. 97117.

8. Plant material from the plant of any of claims 1–7 selected from the group consisting of pollen, seed, seedlings, and cut flowers.

\* \* \* \* \*